US006951571B1

(12) United States Patent
Srivastava

(10) Patent No.: US 6,951,571 B1
(45) Date of Patent: Oct. 4, 2005

(54) VALVE IMPLANTING DEVICE

(76) Inventor: Rohit Srivastava, 8002 Woodbine La., Wausau, WI (US) 54401

( * ) Notice: Subject to any disclaimer, the term of this patent is extended or adjusted under 35 U.S.C. 154(b) by 0 days.

(21) Appl. No.: 10/711,703

(22) Filed: Sep. 30, 2004

(51) Int. Cl.$^7$ ................................................ A61F 2/06
(52) U.S. Cl. .................... 623/1.24; 623/2.1; 623/23.68
(58) Field of Search ............................ 623/1.24, 1.26, 623/23.68, 2.1–2.35; 604/9

(56) References Cited

U.S. PATENT DOCUMENTS

| | | |
|---|---|---|
| 3,671,979 A | 6/1972 | Moulopoulos |
| 3,755,823 A | 9/1973 | Hancock |
| 4,056,854 A | 11/1977 | Boretos |
| 4,253,201 A | 3/1981 | Ross et al. |
| 4,655,771 A | 4/1987 | Walsten |
| 4,733,665 A | 3/1988 | Palmaz |
| 4,856,516 A | 8/1989 | Hillstead |
| 4,994,077 A | 2/1991 | Dobben |
| 5,007,926 A | 4/1991 | Derbyshire |
| 5,123,428 A | 6/1992 | Schwartz |
| 5,163,953 A | 11/1992 | Vince |
| 5,163,955 A | 11/1992 | Calvin et al. |
| 5,332,402 A | 7/1994 | Teitelbaum |
| 5,370,685 A | 12/1994 | Stevens |
| 5,397,351 A | 3/1995 | Pavcnik et al. |
| 5,411,552 A | 5/1995 | Andersen |
| 5,477,864 A | 12/1995 | Davidson |
| 5,571,174 A | 11/1996 | Love |
| 5,653,749 A | 8/1997 | Love |
| 5,824,064 A | 10/1998 | Taheri |
| 5,829,809 A * | 11/1998 | Arney et al. ............. 294/68.21 |
| 5,840,081 A | 11/1998 | Andersen et al. |
| 5,855,597 A | 1/1999 | Jayaraman |
| 5,855,601 A | 1/1999 | Besseler et al. |
| 5,885,601 A | 3/1999 | Sokal |
| 5,925,063 A | 7/1999 | Khosravi |
| 5,954,766 A | 9/1999 | Zadno-Azini et al. |
| 5,957,949 A | 9/1999 | Leonhardt et al. |
| 5,976,179 A | 11/1999 | Inoue |
| 5,980,514 A | 11/1999 | Kupiecki et al. |
| 6,168,592 B1 | 1/2001 | Kupiecki et al. |
| 6,168,614 B1 | 1/2001 | Andersen et al. |
| 6,287,334 B1 | 9/2001 | Moll et al. |
| 6,299,637 B1 | 10/2001 | Shaolian et al. |
| 6,344,041 B1 | 2/2002 | Kupiecki et al. |
| 6,364,901 B1 | 4/2002 | Inoue |
| 6,458,153 B1 | 10/2002 | Bailey et al. |
| 6,540,782 B1 | 4/2003 | Snyders |
| 6,582,462 B1 | 6/2003 | Andersen |
| 6,605,112 B1 | 8/2003 | Moll et al. |

(Continued)

FOREIGN PATENT DOCUMENTS

EP        0820726 A3      1/1998

(Continued)

OTHER PUBLICATIONS

Hufnagel, C.A., Am. J. of Surg., 137:285-300 (1972).

(Continued)

Primary Examiner—Suzette J-J Gherbi
(74) Attorney, Agent, or Firm—Godfrey & Kahn, S.C.

(57) ABSTRACT

Disclosed is a valve implanting device comprising a collapsible frame, inner and outer guide wires removably connected to the collapsible frame, and a plurality of valve flaps attached to the collapsible frame. The collapsible frame is inserted into a patient's femoral vein or artery, guided to a deployment position using the guide wires, expanded using the guide wires, and stabilized using the guide wires to manipulate fixating hubs on the collapsible frame. The collapsible frame includes a central hub, a plurality of spokes, fixating hubs, gripping members, and a plurality of valve flaps.

20 Claims, 6 Drawing Sheets

U.S. PATENT DOCUMENTS

| | | |
|---|---|---|
| 2002/0198586 A1 | 12/2002 | Inoue |
| 2003/0055492 A1 | 3/2003 | Shaolian et al. |
| 2003/0114913 A1 | 6/2003 | Spenser et al. |
| 2003/0130729 A1 | 7/2003 | Paniagua et al. |
| 2003/0153943 A1* | 8/2003 | Michael et al. ............ 606/200 |
| 2003/0231546 A1* | 12/2003 | Bibbo et al. ................ 366/276 |
| 2004/0015230 A1 | 1/2004 | Moll et al |
| 2004/0220610 A1* | 11/2004 | Kreidler et al. ............ 606/200 |

FOREIGN PATENT DOCUMENTS

| | | |
|---|---|---|
| EP | 1010405 A3 | 6/2000 |
| EP | 0820726 B1 | 9/2003 |
| WO | WO 1996 002212 A1 | 2/1996 |
| WO | WO 98 29057 | 7/1998 |
| WO | WO 2000 041652 A1 | 7/2000 |
| WO | WO 2003 047468 A1 | 6/2003 |
| WO | WO 2004 019825 A1 | 3/2004 |

OTHER PUBLICATIONS

Harken et al., J. Thorac & Cdsc. Surg., 40:744-762 (1960).
Lo et al., Trans. Am. Soc. of Art. Int. Organs, 34:839-844 (1988).
Hilbert et al., J. Therac & Cdvs. Surg., 94:419-429 (1987).
Bailey, Steven R., Textbook of Interventional Cardiology, Chap. 75 (1995).
Knudsen et al., Int'l J. of Art. Organs, 16:253-262 (1993).
Knudsen et al., European Heart J. 13:704-708 (1992).
NERAC Search Report.

* cited by examiner

VALVE IMPLANTING DEVICE

BACKGROUND OF THE INVENTION

The present invention relates generally to the field of prosthetic implants, and more particularly to valve implants and methods related thereto.

Valve implants are useful in repairing and introducing desirable blood flow patterns in animal systems. Valve prostheses are usually implanted in one of the channels of the body to replace a natural valve. In particular, heart implants are useful in repairing or replacing damaged heart valves.

As described in the U.S. Pat. No. 6,540,782 to Snyders and U.S. Patent Application 2003/0130729 to Paniagua et al., a human heart has four chambers which alternately expand and contract to pump blood through the vessels of the body. There are four valves in the human heart that serve to direct the flow of blood through the two sides of the heart in a forward direction. On the left (systemic) side of the heart are: 1) the mitral valve, located between the left atrium and the left ventricle, and 2) the aortic valve, located between the left ventricle and the aorta. These two valves direct oxygenated blood coming from the lungs through the left side of the heart into the aorta for distribution to the body. On the right (pulmonary) side of the heart are: 1) the tricuspid valve, located between the right atrium and the right ventricle, and 2) the pulmonary valve, located between the right ventricle and the pulmonary artery. These two valves direct de-oxygenated blood coming from the body through the right side of the heart into the pulmonary artery for distribution to the lungs, where it again becomes re-oxygenated to begin the circuit anew.

Heart valves are passive structures having moveable "leaflets" that simply open and close in response to a differential in the pressures on one side of the valve's leaflets as opposed to the other. The mitral valve has two leaflets, whereas the tricuspid valve has three. The aortic and pulmonary valves are referred to as "semilunar valves" because of the unique appearance of their leaflets, which are more aptly termed "cusps" and are shaped somewhat like a half-moon. The aortic and pulmonary valves each have three cusps.

Besides the leaflets, heart valves further include the valve annulus, which will remain as a roughly circular open ring after the leaflets of a diseased or damaged valve have been removed; papillary muscles which are attached at their bases to the interior surface of the left or right ventricular wall; and multiple chordae tendineae, which couple the valve leaflets or cusps to the papillary muscles. There is no one-to-one chordal connection between the leaflets and the papillary muscles; instead, numerous chordae are present, and chordae from each papillary muscle may attach to more than one of the valve leaflets.

When the left ventricular wall relaxes so that the ventricular chamber enlarges to draw in blood, the leaflets of the mitral valve separate and the valve opens. Oxygenated blood flows in a downward direction through the valve, to fill the expanding ventricular cavity. Once the left ventricular cavity has filled, the left ventricle contracts, causing a rapid rise in the left ventricular cavity pressure. This causes the mitral valve to close while the aortic valve opens, allowing the oxygenated blood to be ejected from the left ventricle into the aorta. The chordae tendineae of the mitral valve prevent the mitral leaflets from prolapsing back into the left atrium when the left ventricular chamber contracts.

The three leaflets, chordae tendineae, and papillary muscles of the tricuspid valve function in a similar manner, in response to the filling of the right ventricle and its subsequent contraction. The cusps of the aortic valve also respond passively to pressure differentials between the left ventricle and the aorta. When the left ventricle contracts, the aortic valve cusps open to allow the flow of oxygenated blood from the left ventricle into the aorta. When the left ventricle relaxes, the aortic valve cusps reapproximate to prevent the blood which has entered the aorta from leaking (regurgitating) back into the left ventricle. The pulmonary valve cusps respond passively in the same manner in response to relaxation and contraction of the right ventricle in moving de-oxygenated blood into the pulmonary artery and thence to the lungs for re-oxygenation. Neither of these semilunar valves has associated chordae tendineae or papillary muscles.

Problems that can develop with heart valves consist of stenosis, in which a valve does not open properly, and/or insufficiency, also called regurgitation, in which a valve does not close properly. In addition to stenosis and insufficiency of heart valves, heart valves may need to be surgically repaired or replaced due to certain types of bacterial or fungal infections in which the valve may continue to function normally, but nevertheless harbors an overgrowth of bacteria (vegetation) on the leaflets of the valve that may embolize and lodge downstream in a vital artery. If such vegetations are on the valves of the left side (i.e., the systemic circulation side) of the heart, embolization may occur, resulting in sudden loss of the blood supply to the affected body organ and immediate malfunction of that organ. The organ commonly affected by such embolization is the brain, in which case the patient suffers a stroke. Thus, surgical replacement of either the mitral or aortic valve (left-side heart valves) may be necessary for this problem even though neither stenosis nor insufficiency of either valve is present. Likewise, bacterial or fungal vegetations on the tricuspid valve may embolize to the lungs resulting in a lung abscess and therefore, may require replacement of the tricuspid valve even though no tricuspid valve stenosis or insufficiency is present.

These problems are sometimes treated by surgical repair of valves, unless, as is often the case, the valves are too diseased to repair and must be replaced. If a heart valve must be replaced, there are currently several options available, and the choice of a particular type of artificial valve depends on factors such as the location of the valve, the age and other specifics of the patient, and the surgeon's experiences and preferences. Currently in the United States over 100,000 defective heart valves are replaced annually, at an approximate cost of $30–50,000 per procedure, and thus it would be desirable if heart valves could be replaced using minimally invasive techniques and without having to repeat the procedure within a matter of years due to the lack of durability of the replacement heart valve. It would be especially advantageous if a defective heart valve could be removed via an endovascular procedure, that is, a procedure where the invasion into the body is through a blood vessel such as the femoral artery. The procedure is then carried out percutaneously and transluminally using the vascular system to convey appropriate devices to the desired location in the body. An example of such a procedure is angioplasty, wherein a catheter carrying a small balloon at its distal end is manipulated through the body's vessels to a point where there is a partial blockage in a vessel. The balloon is expanded to reduce the blockage, in effect enlarge a passage formerly reduced by the blockage, and then the balloon is deflated and the catheter and balloon are removed from the vessel.

Endovascular procedures have substantial benefits both from the standpoint of health and safety as well as cost. Such procedures require minimal invasion of the human body, and there is consequently considerable reduction, and in some instances even elimination, of the use of a general anesthesia, and much shorter hospital stays.

Replacement heart valves can be categorized as artificial mechanical valves, transplanted valves, and tissue valves. Replacement heart valves are designed to optimize hemodynamic performance, thrombogenicity and durability. Another factor taken into consideration is the relative ease of surgical implantation.

Mechanical valves are typically constructed from nonbiological materials such as plastics, metals and other artificial materials which, while durable, are expensive and prone to cause blood clotting which increases the risk of an embolism. Anticoagulants taken to reduce the risk of blood clotting can further complicate the patient's health by increasing the risk of hemorrhage.

Transplanted valves are natural valves taken from cadavers. These valves are typically removed and frozen in liquid nitrogen, and are stored for later use. They are typically fixed in glutaraldehyde to eliminate antigenicity and are sutured in place, typically with a stent.

Artificial tissue valves are valves constructed from animal tissue, such as bovine or porcine tissue. Efforts have also been made at using tissue from the patient for which the valve will be constructed.

Most tissue valves are constructed by sewing the leaflets of pig aortic valves to a stent to hold the leaflets in proper position, or by constructing valve leaflets from the pericardial sac of cows or pigs and sewing them to a stent. The porcine or bovine tissue is chemically treated to alleviate any antigenicity.

One approach to creating artificial tissue valves is described in U.S. Pat. No. 5,163,955 to Calvin, et al. and U.S. Pat. No. 5,571,174 and U.S. Pat. No. 5,653,749 to Love. Using a cutting die, the pericardial tissue is cut into a carefully defined geometric shape, treated with glutaraldehyde, then clamped in a sandwich-fashion between two stent components. This creates a tri-leaflet valve that resembles an aortic or pulmonary valve, having semilunar-type cusps rather than atrioventricular-type leaflets.

U.S. Pat. No. 3,671,979 to Moulopoulos describes an endovascularly inserted conical shaped umbrella-like valve positioned and held in place by an elongated mounting catheter at a supra-annular site to the aortic valve in a nearby arterial vessel. The conical end points toward the malfunctioning aortic valve and the umbrella's distal ends open up against the aorta wall with reverse blood flow, thereby preventing regurgitation.

U.S. Pat. No. 4,056,854 to Boretos describes an endovascularly inserted, catheter mounted, supra-annular valve in which the circular frame abuts the wall of the artery and attached flaps of flexible membrane extend distally in the vasculature. The flaps lie against the artery wall during forward flow, and close inward towards the central catheter to prevent regurgitation during reverse blood flow. The Boretos valve was designed to be positioned against the artery wall during forward flow, as compared to the mid-center position of the Moulopoulos valve, to reduce the stagnation of blood flow and consequent thrombus and embolic formation expected from a valve at mid-center position.

The main advantage of tissue valves is that they do not cause blood clots to form as readily as do the mechanical valves, and therefore, they do not absolutely require systemic anticoagulation. The major disadvantage of tissue valves is that they lack the long-term durability of mechanical valves. Tissue valves have a significant failure rate, usually within ten years following implantation. One cause of these failures is believed to be the chemical treatment of the animal tissue that prevents it from being antigenic to the patient. In addition, the presence of extensive suturing prevents the artificial tissue valve from being anatomically accurate in comparison to a normal heart valve, even in the aortic valve position.

A shortcoming of prior artificial tissue valves has been the inability to effectively simulate the exact anatomy of a native heart valve. Although transplanted human or porcine aortic valves have the gross appearance of native aortic valves, the fixation process (freezing with liquid nitrogen, and chemical treatment, respectively) alters the histologic characteristics of the valve tissue. Porcine and bovine pericardial valves not only require chemical preparation (usually involving fixation with glutaraldehyde), but the leaflets must be sutured to cloth-covered stents in order to hold the leaflets in position for proper opening and closing of the valve. Additionally, the leaflets of most such tissue valves are constructed by cutting or suturing the tissue material, resulting in leaflets that do not duplicate the form and function of a real valve.

Although replacement valves and surgical procedures have been developed to alleviate these conditions, they have significant drawbacks. Many earlier valves require invasive implantation techniques in which the chest is opened, the ribs are spread, the heart is paralyzed, and following cardiopulmonary bypass, the heart is cut open to implant the valve. These invasive techniques are stressful on the patient, and increase the opportunity for infection and slow recovery. As a result, valves which may be implanted with non-invasive techniques have been developed. These valves are implanted by transluminal or endothoracoscopic techniques which reduce many of the drawbacks associated with invasive surgery. However, many of these valves also require the damaged native heart valve be removed prior to implanting the artificial valve. Removing the native valve increases the risk that a portion of the valve will migrate through the body and block vessels downstream from the heart.

Many mechanical and bioprosthetic valves have been developed to replace native heart valves. See C. A. Hufnagel, *Basic Concepts in the Development of Cardiovascular Prostheses*, 137 Am. J. of Surg. at 285–300 (1972). See also D. E. Harken et al., *Partial and Complete Prosthesis in Aortic Insufficiency*, 40 J. Thorac & Cdvsc Surg., no. 6., at 744–62 (1960). These valves include ball-valve prostheses, flap-valve prostheses, polymeric trileaflet synthetic valves, and bioprosthetic valves made from animal allograft tissues such as pig valves and preserved heterologous bovine and porcine pericardial tissue valves. See H. B. Lo et al., *A Tricuspid Polyurethane Heart Valve as an Alternative to Mechanical Prostheses or Bioprostheses,* 34 Trans. Am. Soc. of Art. Int. Organs at 839–44 (1988); and S. L. Hilbert et al., *Evaluation of Explanted Polyurethane Trileaflet Cardiac Valve Prostheses,* 94 J. Thorac & Cdvsc Surg. at 419–29 (1987). Most of the aforementioned valves require open chest surgery and cardio-pulmonary bypass for implantation.

More recently percutaneous and transluminal implantation have been suggested. See Steven R. Bailey, *Percutaneous Expandable Prosthetic Valves Textbook of Interventional Cardiology*, chap. 75 (1995) (referencing work of Andersen et al.) See also Knudsen et al., *Catheter-implanted Prosthetic Heart Valves*, 6 lnt'l J. of Art. Organs, no. 5, at 253–62 (1993); Knudsen et al. *Transluminal Implantation of Artificial Heart Valves. Description of New Expandable Aortic Valve and Initial Results With Implantation by Catheter Technique in Closed Chest Pigs,* 13 European Heart J. at 704–08 (1992); and U.S. Pat. No. 5,411,552 (Andersen). The Andersen device includes a heterologous pig valve mounted in an annular ring. Due to the size of this device, it must be implanted by direct abdominal aortic incision and entry. Further, the Andersen device requires a separate inflating balloon for its deployment.

U.S. Pat. No. 6,540,782 to Snyders describes an artificial heart valve with a frame which has a plurality of peripheral anchors for anchoring the frame in the position between the upstream region and the downstream region and a central portion located between the anchors. The frame generally includes U-shaped stenting elements. By its very nature, however, a U-shaped stenting element may not be easily compressible inside catheter tubing. Further, peripheral anchors attached to the frame may collapse or be dislodged, causing undesirable blood flow, or lack of blood flow altogether. Moreover, Snyders describes a band which generally extends around the frame element. This band is made of biocompatible material, which may cause undesirable thrombogenesis.

U.S. Pat. Application 2003/0130729 to Paniagua describes a percutaneously implantable replacement heart valve comprising a stent member and an artificial valve within the inner cavity of the stent member, where the valve cusps are formed by folding a substantially rectangular sheet of biocompatible tissue material.

PCT application PCT/DE 2003/002669, published as WO 2004/019825 to Figulla et al. describes a heart valve prosthesis fixed to a self-expanding locating support housed in a cartridge which may be connected to a catheter in a folded form. Support hoops are employed in the proximal side of the locating support. Support hoops are released from the cartridge by movement of the cartridge, and are completely deployed by yet another movement of the cartridge.

PCT application PCT/FR00/00051, published as WO 00/41652 to Letac describes a prosthetic valve implantable by catheter or surgical insertion comprising a rigid expandable structure, and a valvular structure which is an integral part of the expandable structure.

PCT application PCT/US95/09013 published as WO 96/02212 to Block et al describes an inflatable cardiovascular valve which may be inflated once deployed in a deflated orientation.

U.S. Pat. No. 5,397,351 to Pavcnik describes an expandable caged poppet for percutaneous implantation in an aortic valve site. However, the size of the Pavcnik device makes percutaneous implantation difficult.

U.S. Pat. No. 5,885,601 to Bessler describes a transluminal valve implantation but does not describe the specific valve construction. The Bessler procedure includes excision, vacuum removal of the native valve, cardio-pulmonary bypass and backflushing of the coronary arterial tree.

U.S. Pat. No. 6,582,462 to Anderson describes a stent made from an expandable cylinder shaped thread structure having several spaced apices. In absence of anchoring devices however, accurate placement and holding in a given position is difficult. See, also, U.S. Pat. No. 6,168,614 (Andersen et al.) and U.S. Pat. No. 5,840,081 (Andersen et al.)

U.S. Pat. Application No. U.S. 2003/0114913 to Spenser et al. describes a valve prosthesis device having a support stent, comprising a deployable construction adapted to be initially crimped in a narrow configuration suitable for catheterization through the body duct to a target location. It is adapted to be deployed by exerting substantially radial forces from within by means of a deployment device to a deployed state in the target location. A valve assembly comprising a flexible conduit having an inlet end and an outlet, made of pliant material attached to the support beams providing collapsible slack portions of the conduit at the outlet, is also described. The support stent is further provided with a plurality of longitudinally rigid support beams of fixed length.

U.S. Pat. No. 6,458,153 to Bailey et al. describes a prosthetic cardiac and venous valve and a catheter device for percutaneous and transluminal valvuloplasty and prosthetic valve implantation.

U.S. Pat. Nos. 3,671,979 and 4,056,854 describe valve prostheses that need either a subsequent activation of the valve or a subsequent repositioning or removal of the valve prosthesis. With these valve prostheses therefore it is impossible for a patient resume a substantially normal life.

U.S. Pat. No. 3,755,823 describes an elastic stent for a cardiac valve prosthesis. However, this valve prosthesis is not designed for implantation in the body by catheterization. Even though this patent contains no detailed explanation, the description indicates that this valve prosthesis is designed for implantation and sewing on by a surgical intervention.

U.S. Pat. Nos. 4,856,516 and 4,733,665 describe different shapes of expandable stents. These stents are expandable by application of a radially outward force coming from a balloon catheter or the like. These stents are made to reinforce the wall when there is a risk that the vessel is closed and/or compressed.

Other percutaneous prosthetic valve devices include the Dobben valve, U.S. Pat. No. 4,994,077. The Dobben valve has a disk-shaped flap threaded on a wire bent like a safety pin to engage the vessel wall and anchor the valve. A second embodiment uses a stent of a cylindrical or crown shape that is made by bending wire into a zigzag shape to anchor the device and attach the flow regulator flap. The device presents significant hemodynamic, delivery, fatigue and stability disadvantages.

U.S. Pat. No. 5,163,953 to Vince describes a valve that has a stent comprised of a toroidal body formed of a flexible coil of wire and a flow-regulation mechanism consisting of a flap of biologic material. Numerous longitudinal extensions within the stent are provided as attachment posts to mount the flow-regulation mechanism. The device requires balloon expansion to deliver to the body orifice. The main shortcoming of this design is delivery profile. Specifically, the device and method put forth will require a 20+ French size catheter (approximately 9 French sizes to accommodate the balloon and 14+ French sizes to accommodate the compressed device) making the device clinically ineffective as a minimally invasive technique. Additionally, the device does not adequately address hemodynamic, stability and anchoring concerns.

U.S. Pat. No. 5,332,402 to Teitelbaum describes a valve that is made of shape memory nitinol and consists of two components. The first component is stent-like and comprised of a meshwork or braiding of nitinol wire similar to that described by Wallsten, U.S. Pat. No. 4,655,771, with trumpet-like distal and proximal flares. The purpose of the stent is to maintain a semi-rigid patent channel through the diseased cardiac valve after initial balloon dilation. The flared ends are intended to maintain the position of the stent component across the valve thereby anchoring the device.

Embodiments for the flow-regulation mechanism include a sliding obturator and a caged ball both which are delivered secondary to the stent portion. The disadvantages of the device are that the flow regulators reduce the effective valve orifice and generate sub-optimal hemodynamic characteristics; fatigue concerns arise from the separate nature of the stent and flow-regulation components; the high metal and exposed metal content increase thrombogenesis, valvular stenosis and chronic anticoagulation concerns; and the separate delivery requirements (although addressing the need for small delivery profile) in addition to any initial valvuloplasty performed increases the time, costs, risks, difficulty and trauma associated with the percutaneous procedure.

U.S. Pat. No. 5,370,685 to Stevens describes a percutaneous valve replacement system for the endovascular removal of a malfunctioning valve followed by replacement with a prosthetic valve. The valve replacement system may include a prosthetic valve device comprised of a stent and cusps for flow regulation such as a fixed porcine aortic valve, a valve introducer, an intraluminal procedure device, a procedure device capsule and a tissue cutter. The devices disclosed indicate a long and complex procedure requiring large diameter catheters. The valve device disclosed will require a large delivery catheter and does not address the key mechanisms required of a functioning valve. Additionally, the device requires intraluminal-securing means such as suturing to anchor the device at the desired location.

U.S. Pat. No. 5,824,064 to Taheri describes an aortic valve replacement combined with an aortic arch graft. The devices and percutaneous methods described require puncture of the chest cavity.

U.S. Pat. No. 5,855,597 to Jayaraman, includes a star-shaped stent and a replacement valve and/or replacement graft for use in repairing a damaged cardiac valve. The device is comprised of a chain of interconnected star-shaped stent segments in the center of which sits a replacement valve. The flow-regulation mechanism consists of three flaps cut into a flat piece of graft material that is rolled to form a conduit in which the three flaps may be folded inwardly in an overlapping manner. An additional flow-regulation mechanism is disclosed in which a patch is (or multiple patches are) sutured to the outside of a conduit which is then pulled inside out or inverted, resulting in the patch(s) residing on the inside of the fully inverted conduit. A balloon catheter is required to assist expansion during delivery. The disadvantages of this design include a lack of a sufficient anchoring mechanism; problematic interference concerns with adjacent tissues and anatomical structures; fatigue concerns associated with the multiplicity of segments, connections and sutures; lack of an adequately controlled and biased flow-regulation mechanism; an uncertain effective valve orifice; difficult manufacture; balloon dilation requirement; complex, difficult and inaccurate delivery and large delivery profile.

U.S. Pat. No. 5,855,601 to Besseler discloses methods and devices for the endovascular removal of a defective heart valve and the replacement with a percutaneous cardiac valve. The device is comprised of a self-expanding stent member with a flexible valve disposed within. The stent member is of a self-expanding cylindrical shape made from a closed wire formed in a zigzag configuration that can be a single piece, stamped or extruded, or formed by welding or otherwise connecting the free ends together. The flow regulation mechanism is comprised of an arcuate portion which contains a slit (or slits) to form leaflets and a cuff portion which is sutured to and encloses the stent. The preferred flow regulator is a porcine pericardium with three cusps. An additional flow regulator is described in which the graft material that comprises the leaflets (no additional mechanisms for flow regulation) extends to form the outer cuff portion and is attached to the stent portion with sutures. The anchoring function is provided by a plurality of barbs carried by the stent (and therefore penetrating the cuff-graft segment). Delivery requires endoluminal removal of the natural valve because the barb anchors will malfunction if they are orthotopically secured to the native leaflets instead of the more rigid tissue at the native annulus or vessel wall. Delivery involves a catheter within which the device and a pusher rod are disposed. The disadvantages of the device are a lack of a well defined and biased flow regulation mechanism; a requirement of anatomic valve removal thereby lengthening the procedure time, increasing difficulty and reducing clinical practicality; trauma induced by the barbs as described above; and the instability of the device and the likelihood of migration if the barbs are omitted.

U.S. Pat. No. 5,925,063 to Khosravi discloses a percutaneous prosthetic valve comprised of a coiled sheet stent similar to that described by Derbyshire, U.S. Pat. No. 5,007,926, to which a plurality of flaps are mounted on the interior surface to form a flow regulation mechanism that may be comprised of a biocompatible material. The disadvantages of this design include problematic interactions between the stent and flaps in the delivery state, lack of clinical data on coiled stent performance, the lack of a detailed mechanism to ensure that the flaps will create a competent one-directional valve, lack of appropriate anchoring means, and the fact that the design requirements imposed by surrounding anatomical structures are ignored.

U.S. Pat. No. 5,954,766 to Zadano-Azizi discloses a device in which flow regulation is provided by a flap disposed within a frame structure capable of taking an insertion state and an expanded state. The preferred embodiment of the flow regulation mechanism is defined by a longitudinal valve body made of a sufficiently resilient material with a slit(s) that extends longitudinally through the valve body. Increased sub-valvular pressure is said to cause the valve body to expand thereby opening the slit and allowing fluid flow therethrough. The valve body extends into the lumen of the body passage, such that increased supra-valvular pressure will prevent the slit from opening, thereby effecting one-directional flow. The device contemplates embedding the frame within the seal or graft material through injection molding, blow molding and insertion molding. The disadvantages of the device include the small effective valve orifice of the flow regulation mechanism, the turbidity caused by the multiple slit mechanisms, the large delivery profile required by the disclosed embodiments, and the lack of acute anchoring means.

U.S. Pat. No. 5,957,949 to Leonhardt describes a valve that is comprised of a tubular graft having radially compressible annular spring portions and a flow regulator, which is preferably a biological valve disposed within. In addition to oversizing the spring stent by 30%, anchoring means is provided by a light-activated biocompatible tissue adhesive located on the outside of the tubular graft that seals to the living tissue. The stent section is comprised of a single piece of superelastic wire formed into a zigzag shape and connected together by crimping tubes, adhesives or welds. A malleable thin-walled, biocompatible, flexible, expandable, woven fabric graft material is connected to the outside of the stent that is in turn connected to the biological flow regulator. Disadvantages of this device include those profile concerns associated with biological valves and unsupported graft-leaflet regulators, a large diameter complex delivery system and method which requires multiple anchoring balloons and the use of a light activated tissue adhesive in addition to any prior valvuloplasty performed, interference with surrounding anatomy and the questionable clinical utility and feasibility of the light activated adhesive.

U.S. Pat. No. 6,299,637 describes a self-expandable prosthetic venous valve, such as for implantation in the deep veins of the leg. The valve is mounted in a support structure, such as a self-expandable tubular wire cage. Deployment catheters and methods are also disclosed.

U.S. Patent to Moll et al. describes a valve prosthesis including a tubular wire frame which presses radially outward against the inner walls of the blood vessel following implantation, to hold the prosthesis in position. Multiple flow-resistive pockets that open and close in response to changes in blood flow direction are attached to the frame to impede the flow of blood in the reverse direction. The prosthesis is implanted using an introducer catheter which holds the prosthesis in a radially-compressed state as the prosthesis is inserted into and positioned within the blood vessel.

PCT application, PCT/EP97/07337, published as WO 98/29057 to Letac et al. describes a valve prosthesis comprising a collapsible valve structure and an expandable frame on which the valve structure is mounted. The valve structure is composed of a valvular tissue compatible with the human body and blood, the valvular tissue being sufficiently supple and resistant to allow the valve structure to be deformed from a closed state to an opened state. The valvular tissue forms a continuous surface and is provided with guiding means formed or incorporated therein, the guiding means creating stiffened zones which induce the valve structure to follow a patterned movement in its expansion to its opened state and in its returning back to its closed state. The valve structure can be extended to an internal cover which is fastened to the lower part of the valve structure to prevent regurgitation.

Yet other known methods currently used for replacing aortic valves and several types of artificial prosthetic devices include mechanical valves that are commonly used in several different designs (single and double flap) manufactured by well-known companies such as St. Jude, Medtronic, Sulzer, and others. Some of the main disadvantages of these devices include a need for permanent treatment by use of anticoagulants, noisy operation, and the need for a large-scale operation to implant.

Overall, each one of these pre-existing stent valve designs has certain disadvantages which are resolved by the present invention. The present invention relates to improvements over existing apparatus as described above, and solutions related to problems raised or not solved thereby.

SUMMARY OF THE INVENTION

The present invention provides a valve implanting device. The device comprises a central hub, a plurality of spokes extending from the central hub, a plurality of fixating hubs, a plurality of gripping members, and a plurality of valve flaps. The central hub is adapted to receive an inner guide wire, and the fixating hubs are adapted to receive outer guide wires. Each of the spokes has a first end engaging the central hub and a second end opposite the first end. Each fixating hub engages one of the spokes at the second end of the spoke. Each of the gripping members engages one of the fixating hubs and an adjacent gripping member, and each valve flap is attached to at least one of the gripping members. The implanting device is ideally collapsible about the central hub.

The central hub, spokes, fixating hubs and gripping members comprise a collapsible frame. Inner and outer guide wires are removably fastened to the collapsible frame, and a plurality of valve flaps are attached to the collapsible frame. The collapsible frame is inserted into a patient's femoral vein or artery in a collapsed shape, guided to a deployment position using the guide wires, expanded using the guide wires, and stabilized using the guide wires to manipulate the fixating hubs on the collapsible frame.

The present invention further contemplates a method for implanting a valve device. The method includes the steps of providing a valve implanting device according to the present invention, collapsing the device about the central hub, inserting the device into a patient's vein or artery, positioning the device in a desired deployment location, expanding the device about the central hub, and stabilizing the device in the desired deployment location.

Advantages and objectives of the present invention include reduced stenosis, ease of heart valve replacement, improved durability, hemodynamic performance, reduced thrombogenicity, relative ease of surgical implantation with minimally invasive techniques, reduced failure rate, appropriate anchoring and positioning means, improved anticoagulation properties, without noisy operations.

Various other features, objects, and advantages of the present invention will be made apparent to those skilled in the art from the following detailed description and accompanying drawings.

DETAILED DESCRIPTION OF THE INVENTION

The present invention provides a prosthetic arterial or venous valve implant which is capable of being delivered using endovascular techniques and may be implanted at an intraarterial, intracardiac or intravenous site without the need for an open surgical procedure. While, the invention is preferably described for implantation via a catheter, the device may also be implanted via open-heart procedures, as described above.

In a preferred embodiment, the present invention provides an arterial valve implant device. In a more preferred embodiment the device is an aortic valve implant. Furthermore, while the device has been described in terms of the most preferred embodiment of an aortic valve implant, one of the ordinary skill in the art, may use and construct this device for use as any arterial or venous valve implant, without departing from the scope of the invention.

The prosthetic valves of the present invention are well-suited for cardiac delivery via a femoral or subclavian artery approach using a delivery catheter, and, depending upon the specific configuration selected, may be deployed within the heart to repair valve defects or disease. One embodiment of the invention provides a chamber-to-vessel (CV) configuration which is particularly well-suited as an aortic valve prosthesis to facilitate blood flow from the left ventricle to the aorta. Another embodiment is a prosthetic valve in a chamber-to-chamber (CC) configuration which is particularly well-adapted for mitral valve replacement.

Common to each of the CV and CC embodiments of the present invention are central and fixating hubs, spokes, gripping members, and valve flaps, which are coupled to the gripping members in a manner which biases the valve flaps so they close upon a zero pressure differential across the valve region.

For purposes of the present invention, references to positional aspects of the present invention will be defined relative to the directional flow vector of blood flow through the implantable device. Thus, the term "proximal" is intended to mean on the inflow or upstream flow side of the device, while "distal" is intended to mean on the outflow or downstream flow side of the device. With respect to the catheter delivery system described herein, the term "proximal" is intended to mean toward the operator end of the catheter, while the term "distal" is intended to mean toward the terminal end or device-carrying end of the catheter.

Figure 1:
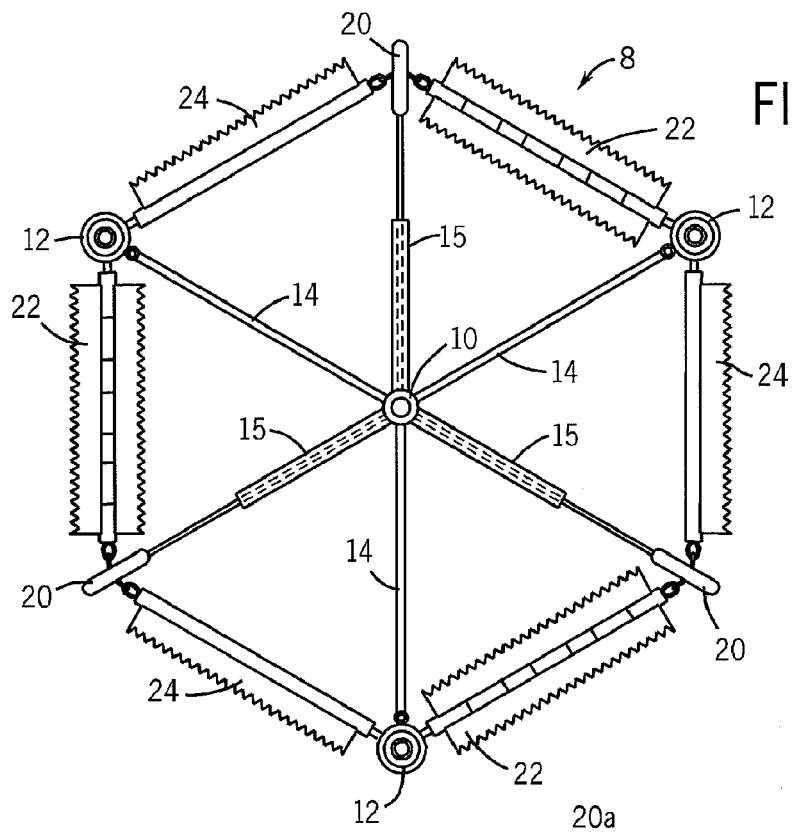
FIG. 1 is a top plan view of a preferred embodiment of the valve implanting device of the present invention.

Referring now to the drawings, FIG. 1 shows a preferred embodiment of the present invention, which provides a top plan view of the implanting device 8 in its open position. FIG. 1 shows a central hub 10 connected to fixating hubs 12 via fixed spokes 14 and expandable spokes 15. Fixed spokes 14 are of a fixed length, and expandable spokes 15 are capable of expanding in length, ideally operating as telescoping members, with a minimum length equal to the length of fixed spokes 14. Each fixating hub 12 is connected to the hub end of a fixating gripping member 22 and the hub end of a stationary gripping member 24. Each fixating gripping member 22 is connected at its other end to the other end of a stationary gripping member 24 by means of a joint 20. The gripping members 22, 24 function to aid in gripping tissue at the deployment location. That is, the gripping members 22, 24 are ideally able to close around and grip a ledge of tissue that was left at the deployment location after the removal of the diseased valve. To that end, the gripping members 22, 24 ideally have jagged, teeth-like edges as shown.

Figure 2:
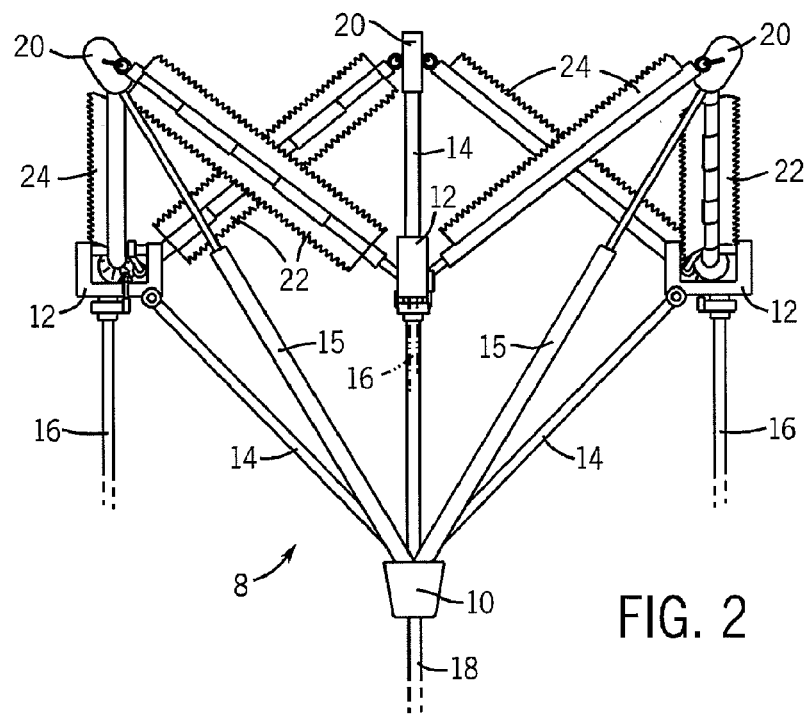
FIG. 2 is a side elevational view of the device of FIG. 1, depicted in a partially open position.
Figure 3A:
FIG. 3a is a side elevational view of the device of FIG. 1, showing guide wires, depicted in a substantially closed position.
Figure 3B:
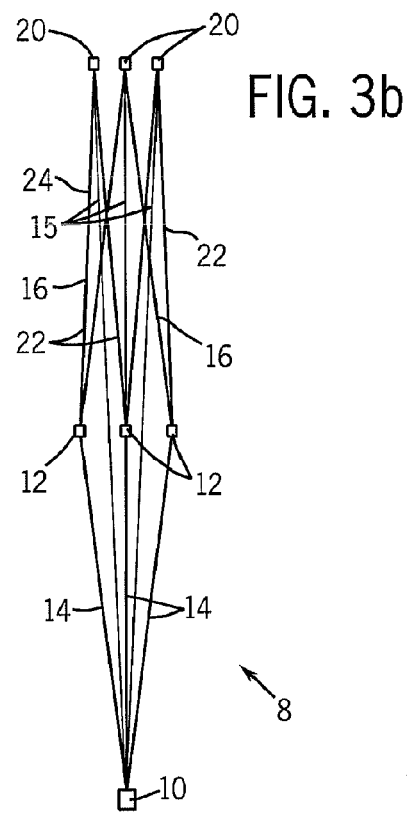
FIG. 3b is a side elevational view of the device of FIG. 1, without guide wires, depicted in a substantially closed position.

Referring now to FIG. 2, the implanting device 8 is shown in a partially open position. The fixed spokes 14 are shown collapsed in an upward direction about central hub 10, expandable spokes 15 are shown partially extended, and collapsed in an upward direction about central hub 10. The fixating gripping members 22 and the stationary gripping members 24 are shown collapsed in a downward direction about joints 20. Outer guide wires 16 are shown extending from each fixating hub 12, and an inner guide wire 18 is shown extending from the central hub 10. FIG. 3a shows a side view of the implanting device 8 in a substantially closed position with the outer and inner guide wires 16, 18. FIG. 3b shows a side view of the implanting device 8 without the outer and inner guide wires 16, 18, for clarity.

Figure 8:
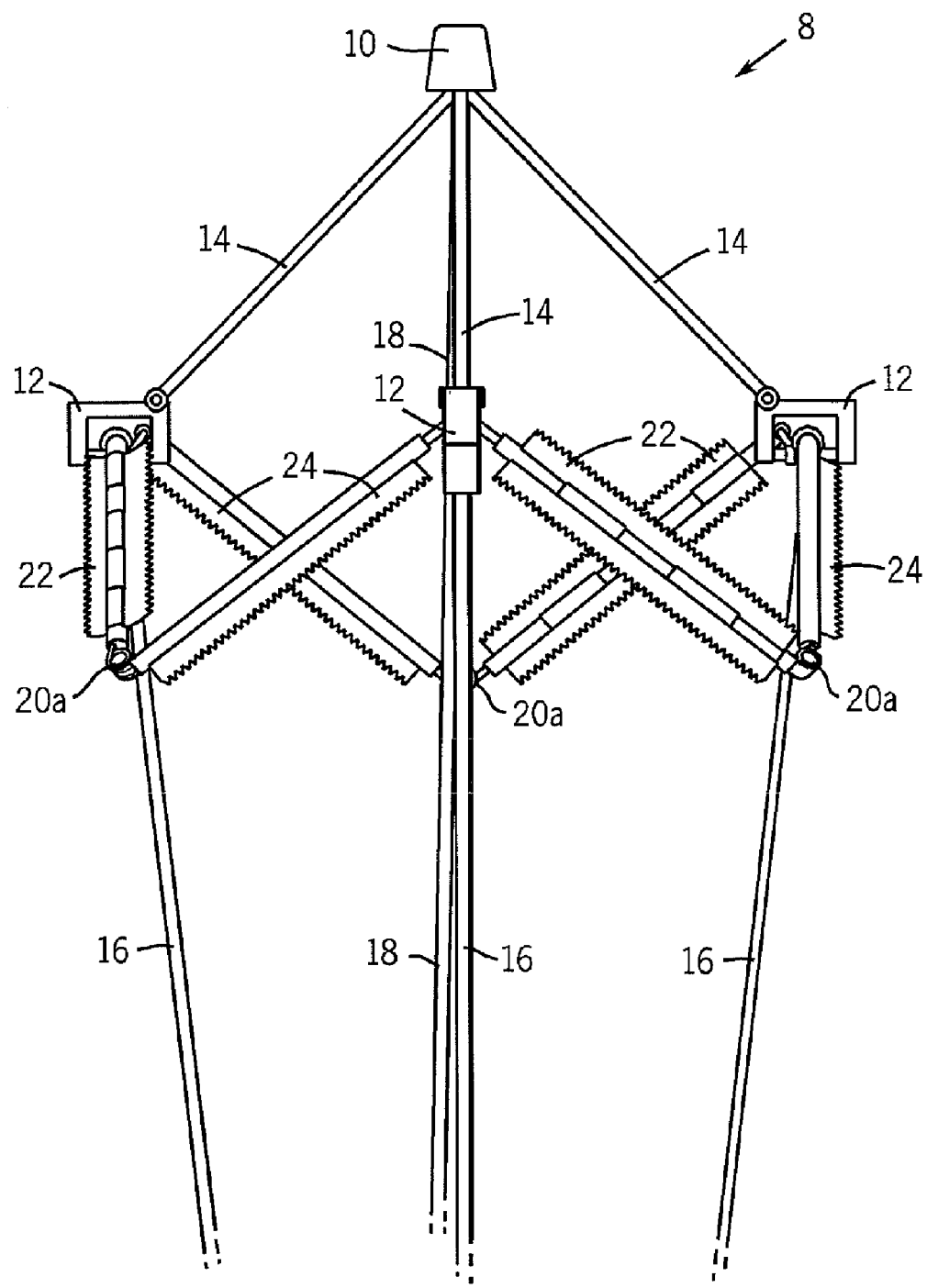
FIG. 8 is a side elevational view of the device of FIG. 7, depicted in a partially open position.
Figure 9A:
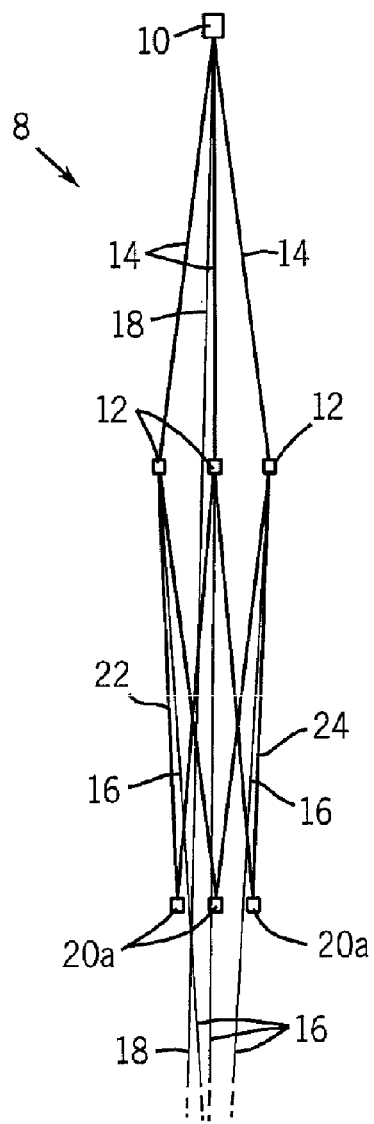
FIG. 9a is a side elevational view of the device of FIG. 7, showing guide wires, depicted in a substantially closed position.

Although FIGS. 2 and 3a show the device collapsed so that joints 20 are at the leading or distal end of the device, the joints and the fixating hubs 12 can pivot either way; thus the device could also be collapsed so that the central hub 10 is at the leading or distal end of the device, as shown in FIGS. 8 and 9a. In a preferred embodiment, the implanting device 8 is inserted in its closed position into a patient's femoral artery or vein and guided to its desired deployment position in the heart. The device can be inserted into a patient's femoral artery for placing the new valve in the aortic valve position, or into a patient's femoral vein for placing the new valve in the mitral position, for which a trans-septal puncture across the atrial septum would be required. When placing the valve in the aortic valve position, the device is inserted so that the joints 20 are leading at the distal end of the device 8 as shown in FIGS. 2 and 3a. When placing the valve in the mitral position, the device is inserted so that the central hub 10 is leading at the distal end of the device 8 as shown in FIGS. 8 and 9a. The manipulation of the device will be made with inner guide wire 18 and outer guide wires 16. When the implanting device 8 is in its desired deployment position, it is opened by holding the outer guide wires 16 in a fixed position and pulling or pushing the inner guide wire 18, causing the implanting device 8 to open in an umbrella-like manner. The inner guide wire 18 will be pushed toward a distal end of the inner guide wire 18 when inserting the device into the aortic valve position (FIG. 2), and pulled toward a proximal end of the inner guide wire 18 when inserting the device into the mitral position (FIG. 8). The implanting device 8 is then fixed in the open position using the fixating hubs 12 and fixating gripping members 22.

Figure 4:
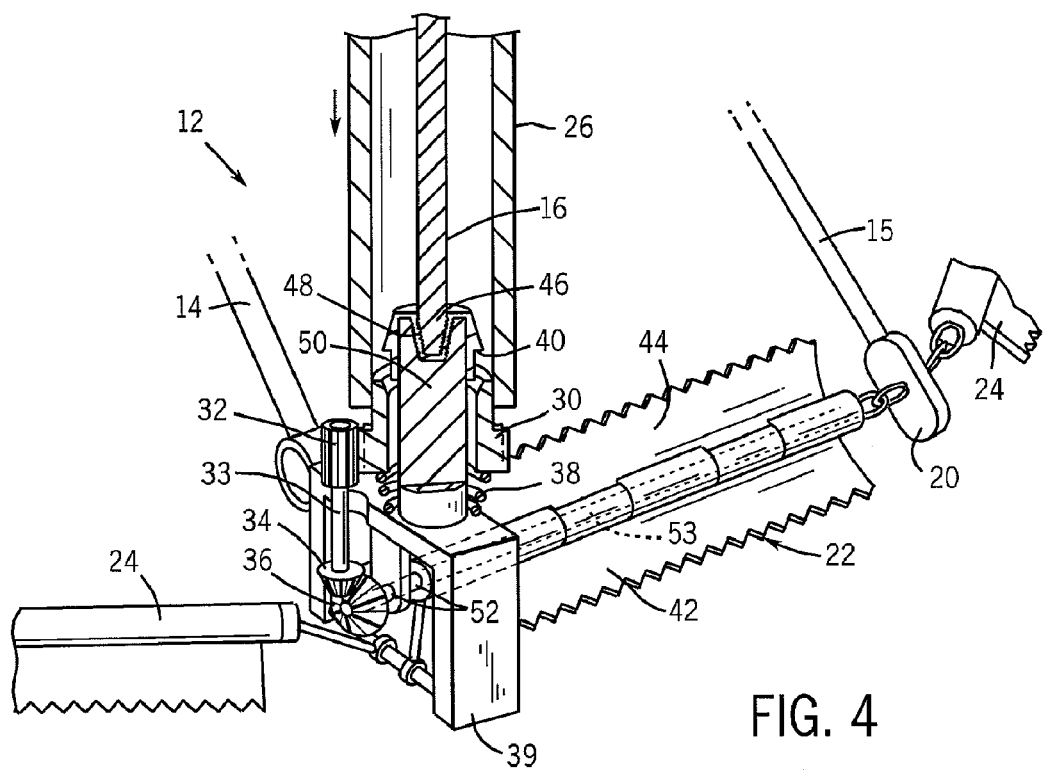
FIG. 4 is an enlarged partial cross-sectional view of a fixation hub assembly of the device of FIG. 1, showing the fixating gripping members in an open position.
Figure 5:
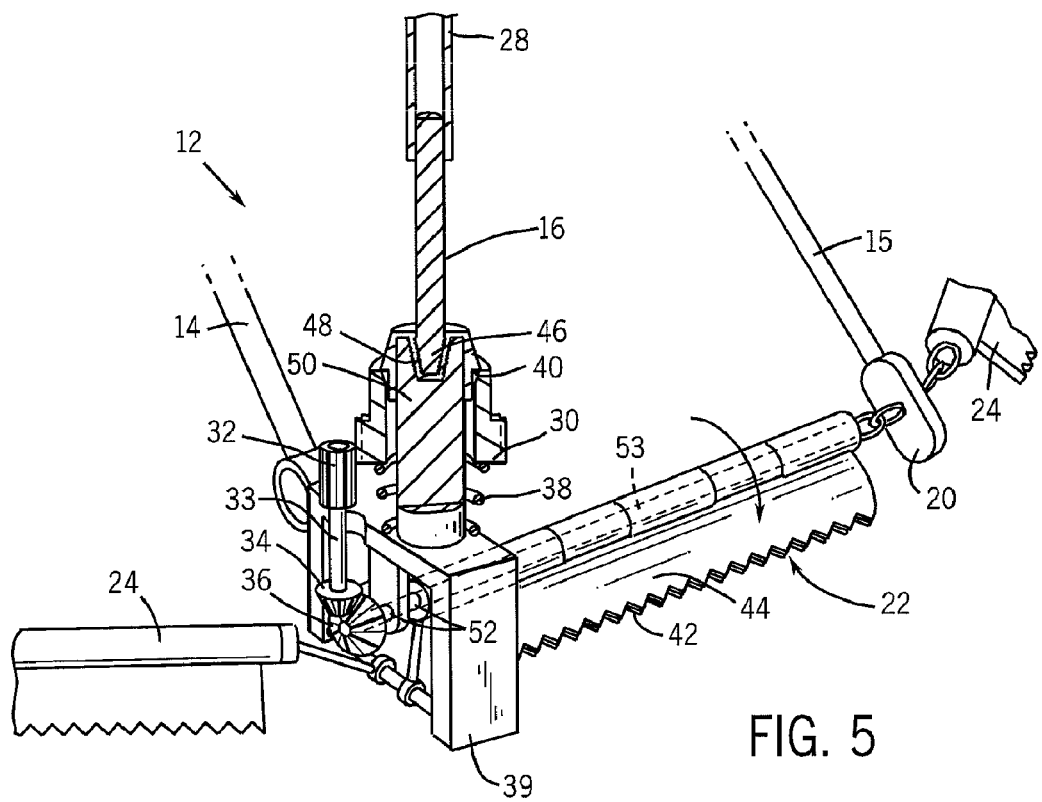
FIG. 5 is an enlarged partial cross-sectional view of a fixation hub assembly of the device of FIG. 1, showing the fixating gripping members in a closed position.

FIGS. 4 and 5 show an enlarged cross-sectional detail of a fixating hub 12. FIGS. 4 and 5 show a removably connected first end 46 of an outer guide wire 16 fastened to a pocket 48 of the body 50 of the fixating hub 12. The first end 46 of the outer guide wire 16 is preferably removably connected to the pocket 48 using a threaded connection as shown in FIGS. 4 and 5. A first gear 30 is rotatably mounted around the body 50 and meshes with a second gear 32. The second gear 32 is connected via transfer shaft 33 to a third gear 34, that in turn meshes with a fourth gear 36 to turn a first shaft 52. The first shaft 52 is connected, ideally using hinges (not shown) to allow collapse of the device, to a second shaft 53 that extends through the longitudinal axis of fixating gripping member 22. The rotating portion 44 of the fixating gripping member 22 is rigidly fixed to the second shaft 53 and thus rotates with the second shaft 53. The fixed portion 42 of the fixating gripping member 22 is mounted around the second shaft 53 to allow relative motion between the second shaft 53 and the fixed portion 42 of the fixating gripping member 22 so that the fixed portion 42 stays in a fixed position when the second shaft 53 rotates. The fixed portion 42 of the fixating gripping member 22, the second shaft 53, and the rotating portion 44 of the fixating gripping member 22 ideally operate like a door hinge mechanism. The fixating gripping member 22 in FIG. 4 is shown in an open position, and the fixating gripping member 22 in FIG. 5 is shown in a closed position.

To secure or fix the implanting device using the fixating hub 12 shown in FIGS. 4 and 5, a first sleeve 26 having an inner diameter slightly larger than the outer diameter of the first gear 30 is passed over the proximal end (not shown) of the outer guide wire 16 and inserted into the patient's femoral artery or vein. The first sleeve 26 surrounds the outer guide wire 16 and follows its path to the fixating hub 12. As shown in FIG. 4, the first sleeve 26 engages the first gear 30, ideally as a wrench and nut mechanism, such that turning the first sleeve 26 rotates the first gear 30. The first sleeve 26 is turned until the rotating portion 44 of the fixating gripping member 22 is in its closed position, as shown in FIG. 5. Once the rotating portion 44 of the fixating gripping member 22 is in its closed position, as shown in FIG. 5, the first sleeve 26 can be removed from the patient. When the first sleeve 26 is removed, spring 38, which is restrained on one end by the fixating hub frame 39, pushes the first gear 30 out to notch 40, as shown in FIG. 5, to secure the fixating gripping member 22 in its closed position and stabilizing the device.

Further, a second sleeve 28 having an inner diameter slightly larger than the outer diameter of the outer guide wire 16 is passed over the proximal end (not shown) of the outer guide wire 16, and is inserted into the patient's femoral artery or vein. The second sleeve 28 surrounds the outer guide wire 16 and follows its path to the fixating hub 12. As shown in FIG. 5, the second sleeve 28 engages the outer guide wire 16, ideally as a wrench and nut mechanism, so that turning the second sleeve 28 rotates the outer guide wire 16, thereby disconnecting it from the pocket 48, preferably though not necessarily by unthreading. The second sleeve 28 and the outer guide wire 16 can then be removed from the patient.

The process of inserting a first sleeve 26 to secure a fixating gripping member 22 and inserting a second sleeve 28 to remove the outer guide wire 16 is then repeated for the remaining two fixating hubs 12 to secure the corresponding fixating gripping members 22 in their closed positions and to remove the remaining two outer guide wires 16, allowing the implanting device 8 to stay in place in the desired deployment location. A second sleeve 28 surrounding the inner guide wire 18 is then inserted to remove the inner guide wire 18 from the patient, ideally in an analogous manner.

Figure 6A:
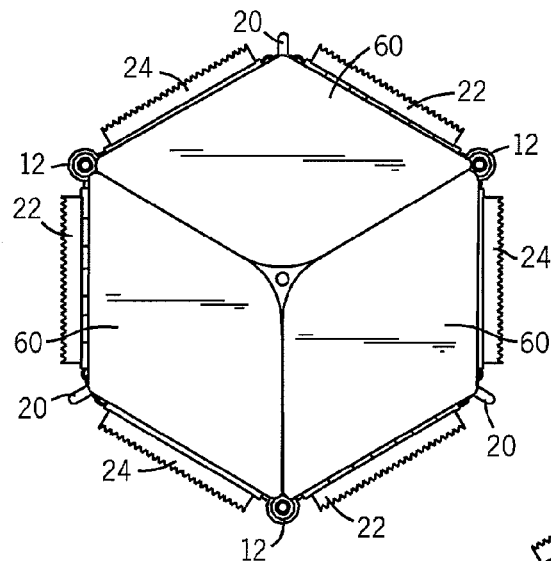
FIG. 6a is a top plan view of the device of FIG. 1 but now including valve flaps, with the valve flaps shown in a closed position.
Figure 6B:
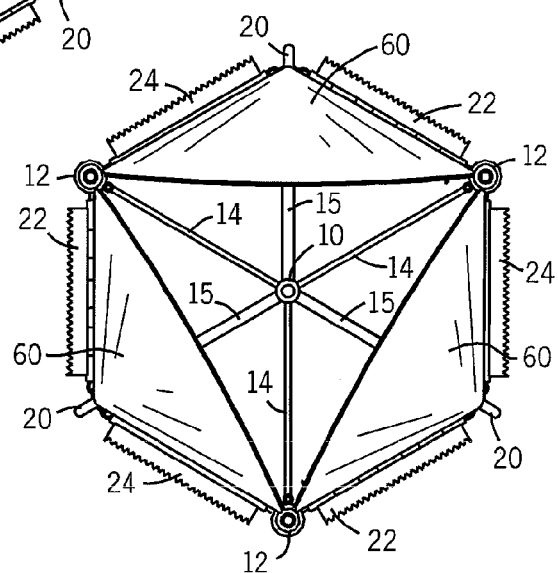
FIG. 6b is a top plan view of the device of FIG. 1 including valve flaps with the valve flaps in an open position.
Figure 6C:
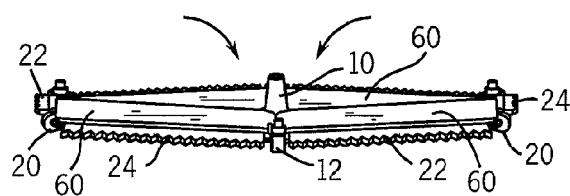
FIG. 6c is a side elevational view of the device of FIG. 1 but now including valve flaps, with the valve flaps shown in a closed position.
Figure 6D:
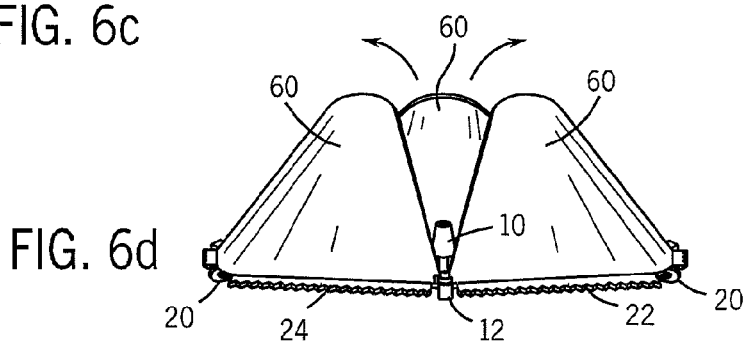
FIG. 6d is a side elevational view of the device of FIG. 1 but now including valve flaps, with the valve flaps shown in an open position.

In practice, the implanting device 8 will have new valve flaps 60 attached to the fixating gripping members 22 and the stationary gripping members 24 prior to insertion into the femoral artery or vein, as shown in FIGS. 6a–6d, such that the valve flaps 60 collapse and expand with the implanting device 8. FIG. 6a shows the device 8 in its expanded position, with the valve flaps 60 in a closed position, and FIG. 6b shows the device 8 in its closed position and the valve flaps 60 in an open position. Fixed spokes 14 and expandable spokes 15 can be seen behind the valve flaps 60. FIGS. 6c and 6d show a side view of the device 8 in its expanded position, FIG. 6c showing the valve flaps 60 in a closed position and FIG. 6c showing the valve flaps 60 in an open position.

A wide range of biologically based valves made of natural valve material or composed of biological materials such as pericardial tissue may be used. These are made and marketed by well-known companies such as Edwards Lifesciences, Medtronic, Sulzer, and Sorin. Other materials such as heterologous animal pericarium (e.g. bovine or porcine pericardium) or autologous tissue-engineered substrates can also be used without departing from the scope of the present invention. Other preferred embodiments may include biocompatible, radiopaque, elastic material such as silicone rubber, polyureathane or PTFE.

Figure 7:
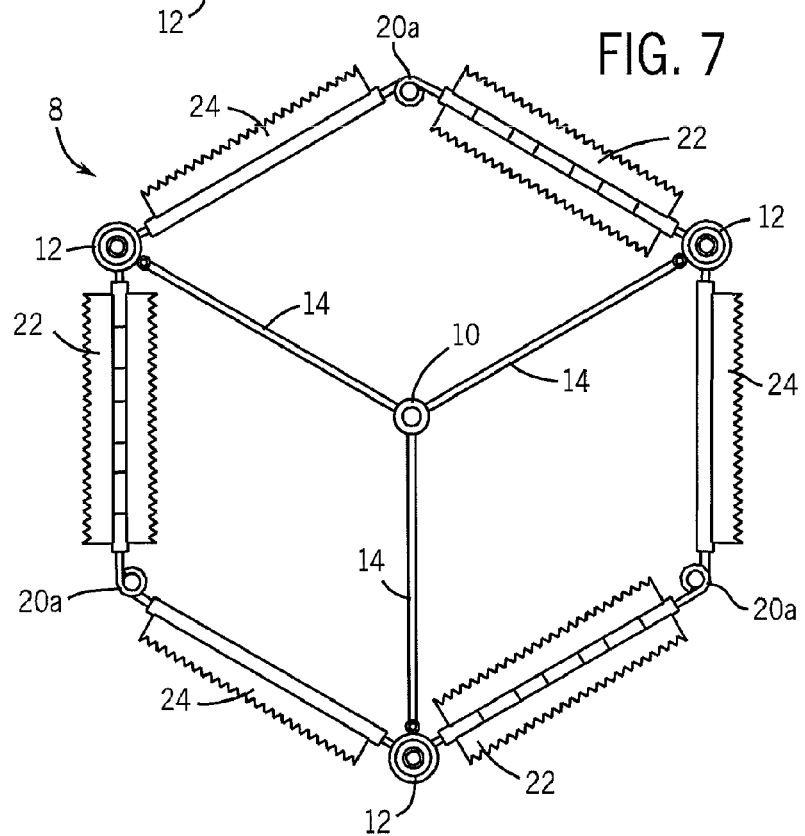
FIG. 7 is a top plan view of another embodiment of the valve implanting device of the present invention.

FIG. 7 shows another embodiment of the implanting device of the present invention. In FIG. 7, a central hub 10 is connected to fixating hubs 12 via fixed spokes 14. Each fixating hub 12 is connected to a fixating gripping member 22 and a stationary gripping member 24. The fixating gripping members 22 and the stationary gripping members 24 are connected with joints 20a. Joints 20a are ideally hinges that will allow the gripping members 22, 24 to expand outward as the device is deployed, but will not allow the gripping members 22, 24 to collapse inward. Because of this restriction in joints 20a, the expandable spokes 15 shown in connection with the other embodiment are not necessary in this embodiment.

Figure 9B:
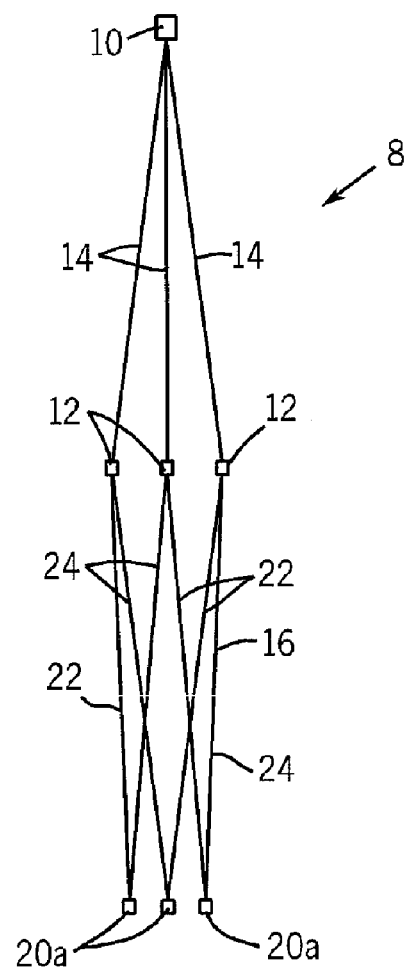
FIG. 9b is a side elevational view of the device of FIG. 7, without guide wires, depicted in a substantially closed position.

FIG. 8 shows a side view of the implanting device of FIG. 7 in a partially open position. The fixed spokes 14 are shown collapsed in a downward direction about central hub 10, and the fixating gripping members 22 and the stationary gripping members 24 are shown collapsed in an upward direction about joints 20a. Outer guide wires 16 are shown extending from each fixating hub 12, and an inner guide wire 18 is shown extending from the central hub 10. FIG. 9a shows a side view of the implanting device of FIG. 7 in a substantially closed position with the outer and inner guide wires 16, 18, and FIG. 9b shows a side view of the implanting device of FIG. 7 without the outer and inner guide wires 16, 18. Although the device in FIGS. 8 and 9a is shown collapsed so that the central hub is at the distal end of the device 8, the device could also be collapsed so that the joints 20a are at the distal end of the device 8, as shown in FIGS. 2 and 3a.

Advantages of the present invention include reduced stenosis, ease of heart valve replacement, improved durability, hemodynamic performance, reduced thrombogenicity, relative ease of surgical implantation with minimally invasive techniques, reduced failure rate, appropriate anchoring and positioning means, improved anticoagulation properties, without noisy operations.

All references, including patents disclosed in the present invention are incorporated herein by for all purposes. Accordingly, materials, methods and techniques disclosed in these references may be used for the construction and invasive or non-invasive implantation of the valve implanting device without departing from the scope of the invention.

While the invention has been described with reference to preferred embodiments, it is to be understood that the invention is not intended to be limited to the specific embodiments set forth above. It is recognized that those of skill in the art will appreciate certain substitutions, alterations, modifications, and omissions may be made without parting from the spirit or intent of the invention. Accordingly, the foregoing description is meant to be exemplary only, the invention is to be taken as including all reasonable equivalents to the subject matter of the invention as defined by the following claims, and should not limit the scope of the invention.

What is claimed is:

1. A biocompatible prosthetic valve implanting device comprising:
   a central hub configured to receive an inner guide wire;
   a plurality of spokes extending from the central hub, each spoke having a first end engaging the central hub and a second end opposite the first end;
   a plurality of fixating hubs, each fixating hub engaging one of the spokes at the second end of the spoke, and each fixating hub configured to receive an outer guide wire;
   a plurality of gripping members, each gripping member engaging one of the fixating hubs and an adjacent gripping member; and
   a plurality of implantable biocompatible valve flaps, each valve flap attached to at least one of the gripping members.

2. The implanting device of claim 1, wherein the device is collapsible about the central hub.

3. The implanting device of claim 1, wherein the plurality of spokes includes at least three spokes.

4. The implanting device of claim 1, wherein the plurality of spokes includes at least six spokes.

5. The implanting device of claim 1, wherein the plurality of spokes includes at least two types of spokes.

6. The implanting device of claim 1, wherein the plurality of spokes includes fixed spokes and expandable spokes.

7. The implanting device of claim 6, wherein the fixed spokes have a fixed length.

8. The implanting device of claim 7, wherein the expandable spokes have a minimum length equal to the fixed length of the fixed spokes.

9. The implanting device of claim 6, wherein the fixating hubs engage fixed spokes.

10. The implanting device of claim 1, wherein at least one of the gripping members has a fixed portion and a rotating portion.

11. The implanting device of claim 10, wherein the fixating hubs are manipulated to rotate the rotating portions of the gripping members.

12. The implanting device of claim 10, wherein rotating the rotating portion of each of the gripping members stabilizes the implanting device.

13. The implanting device of claim 1, wherein each of the fixating hubs includes a body, a first gear engaging a second gear, the second gear engaging a third gear, and the third gear engaging a fourth gear, a spring biasing the first gear toward a notch, a first shaft engaging the fourth gear, and a second shaft engaging the first shaft and a rotating portion of one of the gripping members.

14. A method for implanting a valve device, the method comprising:
   providing a valve implanting device having (i) a central hub adapted to receive an inner guide wire, (ii) a plurality of spokes extending from the central hub, each spoke having a first end engaging the central hub and a second end opposite the first end, (iii) a plurality of fixating hubs, each fixating hub engaging one of the spokes at the second end of the spoke, and each fixating hub adapted to receive an outer guide wire, (iv) a plurality of gripping members, each gripping member engaging one of the fixating hubs and an adjacent gripping member, (v) a plurality of valve flaps, each valve flap attached to at least one of the gripping members, (vi) an inner guide wire removably fastened to the central hub, and (vii) an outer guide wire removably fastened to each of the fixating hubs;
   collapsing the device about the central hub;
   inserting the device into a patient's vein or artery;
   positioning the device in a desired deployment location;
   expanding the device about the central hub; and
   stabilizing the device in the desired deployment location.

15. The method of claim 14, wherein the inner and outer guide wires are used to position the device in the desired deployment location.

16. The method of claim 14, wherein expanding the device includes holding the outer guide wires in a fixed position and pushing the inner guide wire toward a distal end of the inner guide wire.

17. The method of claim 14, wherein expanding the device includes holding the outer guide wires in a fixed position and pulling the inner guide wire toward a proximal end of the inner guide wire.

18. The method of claim 14, wherein stabilizing the device includes manipulating the fixating hubs to rotate a rotating portion of each of the gripping members.

19. The method of claim 14, wherein stabilizing the device includes removing the inner and outer guide wires from the device and from the patient's vein or artery.

20. A valve implanting device comprising:
   a collapsible frame including (i) a central hub adapted to receive an inner guide wire, (ii) a plurality of spokes extending from the central hub, each spoke having a first end engaging the central hub and a second end opposing the first end, (iii) a plurality of fixating hubs, each fixating hub engaging one of the spokes at the second end of the spoke, and each fixating hub adapted to receive an outer guide wire, and (iv) a plurality of gripping members, each gripping member engaging one of the fixating hubs and an adjacent gripping member;
   an inner guide wire removably fastened to the central hub of the frame;
   an outer guide wire removably fastened to each of the fixating hubs of the frame;
   a plurality of valve flaps, each valve flap attached to at least one of the gripping members; and
   wherein the collapsible frame is configured to be inserted into a patient's femoral vein or artery in a collapsed shape, guided to a desired deployment position using the inner and outer guide wires, expanded using the inner and outer guide wires, and stabilized in the desired position using the guide wires to manipulate the fixating hubs.

* * * * *